US012797145B2

(12) United States Patent
Boisvert et al.

(10) Patent No.: US 12,797,145 B2
(45) Date of Patent: Nov. 17, 2026

(54) REVISION ROBOTICS

(71) Applicant: Orthosoft ULC, Montreal (CA)

(72) Inventors: Olivier Boisvert, Montreal (CA); Ryan Lundquist, Norman, OK (US); Yann Facchinello, Prévost (CA); Eric Greber, Thibodaux, LA (US)

(73) Assignee: Orthosoft ULC, Montreal (CA)

( * ) Notice: Subject to any disclaimer, the term of this patent is extended or adjusted under 35 U.S.C. 154(b) by 20 days.

(21) Appl. No.: 18/910,725

(22) Filed: Oct. 9, 2024

(65) Prior Publication Data

US 2025/0032205 A1 Jan. 30, 2025

Related U.S. Application Data

(63) Continuation of application No. 16/988,090, filed on Aug. 7, 2020, now Pat. No. 12,137,996.
(Continued)

(51) Int. Cl.
*A61B 34/32* (2016.01)
*A61B 17/00* (2006.01)
(Continued)

(52) U.S. Cl.
CPC .............. *A61B 34/32* (2016.02); *A61B 34/20* (2016.02); *A61F 2/461* (2013.01); *A61B 2017/00115* (2013.01); *A61B 2034/105* (2016.02); *A61B 2034/2055* (2016.02); *A61B 2034/2065* (2016.02)

(58) Field of Classification Search
CPC ... A61B 34/32; A61B 34/20; A61B 2034/105; A61B 2034/2055; A61B 2034/2065; A61B 2017/00115; A61F 2/461
See application file for complete search history.

(56) References Cited

U.S. PATENT DOCUMENTS 5,769,092 A 6/1998 Williamson, Jr.
10,194,991 B2 2/2019 Bonny et al.
(Continued)

FOREIGN PATENT DOCUMENTS

EP 1870053 B1 12/2009
WO WO-2016094298 A1 * 6/2016 ............. A61B 34/10
(Continued)

OTHER PUBLICATIONS

"U.S. Appl. No. 16/988,090, Advisory Action mailed May 23, 2024", 6 pgs.

(Continued)

*Primary Examiner* — Kevin T Truong
*Assistant Examiner* — Diana Jones
(74) *Attorney, Agent, or Firm* — SCHWEGMAN LUNDBERG & WOESSNER, P.A.

(57) ABSTRACT

Systems and methods may be used for performing a robotic revision knee arthroplasty. For example, a robotic surgical device may be used to perform a cut. The cut may be planned to remove an existing implant based on information about the existing implant (e.g., reference points on the existing implant, an implant type, a maker of the implant, degradation information about the implant, a failure reason for the implant, or the like). In an example, a new plan may be developed for a new implant to replace the existing implant.

18 Claims, 13 Drawing Sheets

Related U.S. Application Data

(60) Provisional application No. 62/884,814, filed on Aug. 9, 2019.

(51) Int. Cl.

| | |
|---|---|
| ***A61B 34/10*** | (2016.01) |
| ***A61B 34/20*** | (2016.01) |
| ***A61F 2/46*** | (2006.01) |

(56) References Cited

U.S. PATENT DOCUMENTS

| | | | |
|---|---|---|---|
| 10,265,127 | B2 | 4/2019 | Jaramaz et al. |
| 10,716,630 | B2 | 7/2020 | Krebs et al. |
| 10,932,866 | B1 | 3/2021 | Bonny et al. |
| 11,364,081 | B2 | 6/2022 | Dees, Jr. |
| 11,478,362 | B2 | 10/2022 | Thompson et al. |
| 12,137,996 | B2 | 11/2024 | Boisvert et al. |
| 12,150,657 | B2 | 11/2024 | Greber |
| 2007/0270680 | A1 | 11/2007 | Sheffer et al. |
| 2009/0102844 | A1 | 4/2009 | Deparis |
| 2017/0265945 | A1 | 9/2017 | Jaramaz et al. |
| 2017/0360509 | A1 | 12/2017 | Bonny et al. |
| 2018/0014891 | A1* | 1/2018 | Krebs .................. A61B 90/361 |
| 2018/0116739 | A1 | 5/2018 | Gogarty et al. |
| 2019/0272917 | A1* | 9/2019 | Couture ................. G06N 20/00 |
| 2020/0138518 | A1 | 5/2020 | Lang |
| 2020/0222206 | A1 | 7/2020 | Elliot |
| 2021/0038328 | A1 | 2/2021 | Boisvert et al. |
| 2023/0013210 | A1 | 1/2023 | Facchinello et al. |

FOREIGN PATENT DOCUMENTS

| | | | | |
|---|---|---|---|---|
| WO | WO-2019135805 | A1 * | 7/2019 | ........... A61F 5/3761 |
| WO | WO-2020163314 | A1 | 8/2020 | |
| WO | WO-2021067922 | A1 | 4/2021 | |

OTHER PUBLICATIONS

"U.S. Appl. No. 16/988,090, Final Office Action mailed Feb. 23, 2024", 11 pgs.
"U.S. Appl. No. 16/988,090, Non Final Office Action mailed Sep. 27, 2023", 9 pgs.
"U.S. Appl. No. 16/988,090, Notice of Allowance mailed Jul. 9, 2024", 10 pgs.
"U.S. Appl. No. 16/988,090, Response filed Apr. 22, 2024 to Final Office Action mailed Feb. 23, 2024", 8 pgs.
"U.S. Appl. No. 16/988,090, Response filed May 20, 2024 to Final Office Action mailed Feb. 23, 2024", 9 pgs.
"U.S. Appl. No. 16/988,090, Response filed Jul. 31, 2023 to Restriction Requirement mailed May 31, 2023", 6 pgs.
"U.S. Appl. No. 16/988,090, Response filed Dec. 27, 2023 to Non Final Office Action mailed Sep. 27, 2023", 7 pgs.
"U.S. Appl. No. 16/988,090, Restriction Requirement mailed May 31, 2023", 7 pgs.
"Canadian Application Serial No. 3,167,940, Examiners Rule 86(2) Requisition mailed Oct. 5, 2023", 11 pgs.
"Canadian Application Serial No. 3,167,940, Response Filed Feb. 1, 2024 to Examiners Rule 86(2) Requisition mailed Oct. 5, 2023", 21 pgs.
"European Application Serial No. 22185819.4, Extended European Search Report mailed Nov. 29, 2022", 10 pgs.
"European Application Serial No. 22185819.4, Response filed Jul. 25, 2023 to Extended European Search Report mailed Nov. 29, 2022", 27 pgs.
Giordano, MD, Gerard, et al., "ExactechGPS RTKA Operative Technique", Exactech, Inc. 712-32-30 Rev. B 0621, (2021), 50 pgs.
"European Application Serial No. 22185819.4, Communication Pursuant to Article 94(3) EPC mailed Apr. 16, 2025", 9 pgs.
"U.S. Appl. No. 17/864,682, Non Final Office Action mailed May 30, 2025", 16 pgs.
"European Application Serial No. 22185819.4, Response Filed Jul. 16, 2025 to Communication Pursuant to Article 94(3) EPC mailed Apr. 16, 2025", 64 pgs.
"Canadian Application Serial No. 3, 167,940, Examiners Rule 86(2) Report mailed Jul. 14, 2025", 11 pgs.
"U.S. Appl. No. 17/864,682, Response filed Aug. 22, 2025 to Non Final Office Action mailed May 30, 2025", 18 pgs.
"U.S. Appl. No. 17/864,682, Examiner Interview Summary mailed Aug. 25, 2025", 3 pgs.
"U.S. Appl. No. 17/864,682, Notice of Allowance mailed Nov. 4, 2025", 5 pgs.
"Canadian Application Serial No. 3,167,940, Response Filed Nov. 11, 2025 to Examiners Rule 86(2) Report mailed Jul. 14, 2025", 14 pgs.

* cited by examiner

300A

300B

700

REVISION ROBOTICS

CLAIM OF PRIORITY

This application is a continuation of U.S. patent application Ser. No. 16/988,090, filed on Aug. 7, 2020, which claims the benefit of priority to U.S. Provisional Application No. 62/884,814, filed Aug. 9, 2019, titled "REVISION ROBOTICS"; each of which is hereby incorporated herein by reference in its entirety.

BACKGROUND

An implant revision surgery is a process by which an existing implant is removed to be replaced by a new implant. However, due to the bond between the implant to be removed and the bone, the bone is often damaged during implant removal. As a result, the subsequent positioning and installation of a replacement implant may lack precision due to damaged bone surfaces. For instance, in knee revision surgery, machining of the bone surfaces using conventional cutting blocks may lack precision as conventional bone landmarks used for defining the orientation of the cutting block may be altered or removed during the removal of the implant.

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. Many conventional techniques (that do not use a robot, for example) may result in errors or may lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for performing a revision using a robotic surgical device are described herein. These systems and methods herein may be used for performing a robotic revision knee arthroplasty.

Revision surgery includes removing a previous implant and placing a new implant. The systems and methods described herein use a robotic surgical device to assist in portions of the revision surgical process. For example, a robotic surgical device may be used for measurements, as a cut guide, to autonomously make cuts, as a force assist device, or the like. The robotic surgical device may be used during planning, removal of the existing implant, replanning for a new implant, or the placement of the new implant. In particular, the robotic surgical device may be used to perform a cut to remove the existing implant, prepare a canal or surface, or place the new implant.

Use of the robotic surgical device may improve precision, for example on cutting surfaces or to adhere more closely to a plan or replan. In an example, cuts may be planned to remove an existing implant, an intraoperative reassessment may occur, and a robotic surgical device may be made to perform clean up cuts. In another example technique, a robotic surgical device may be used to perform a cut to remove an existing implant, perform clean up cuts, a redigitizing or repainting of a surface (e.g. a remap) may occur with a replan on new bone, and the robotic surgical device may perform potential clean up cuts or clean up burring. In these examples or with other example techniques, predictive analytics or a bone atlas may be used to plan or replan the bone surfaces, and a new implant may be implanted.

Figure 1:
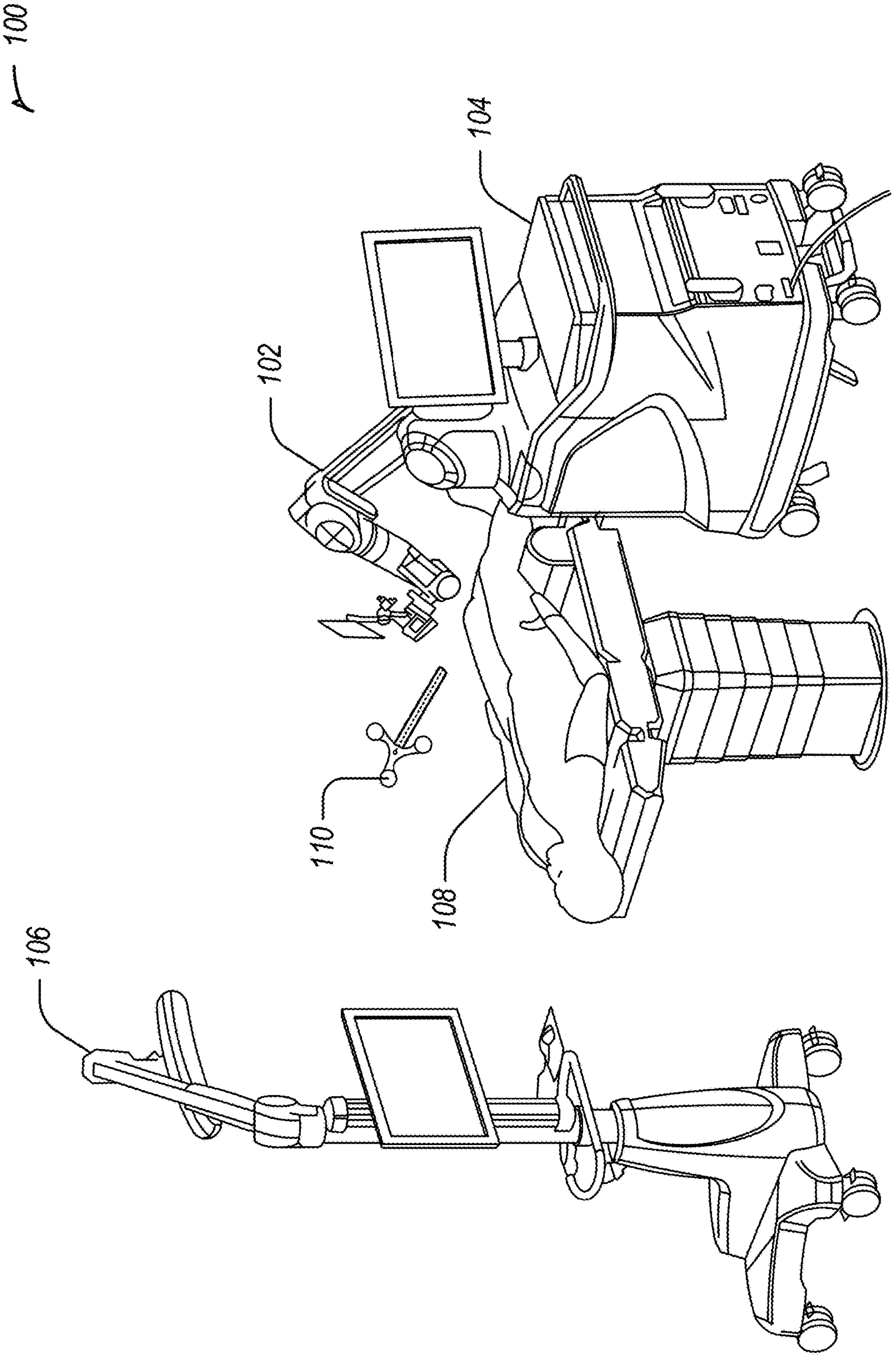
FIG. 1 illustrates a robotic surgical system including a robotic surgical device (e.g., a robot or a robotic arm) and a computer (e.g., a device having a processor) in accordance with at least one example of this disclosure.

FIG. 1 illustrates a robotic surgical system 100 including a robotic surgical device 102 (e.g., a robot or a robotic arm) and a computing device 104 (e.g., a device having a processor) in accordance with at least one example of this disclosure. In an example, the robotic surgical device 102 and the computing device 104 may be coupled, such as communicatively coupled or physically connected.

The system 100 optionally includes an optical navigation system 106, which may detect a location of an optical navigation device 110. The system 100 is shown in relation to a patient 108. The patient 108 may be undergoing a revision procedure, for example to remove an existing implant and optionally receive a new implant. The robotic surgical device 102 may be used to perform aspects of the revision procedure.

In an example, a bone or bones of the patient 108 may be modeled before an existing implant is removed. The current bone and implant model may be in a virtual 3D format. For example, frontal and lateral images of the bone and implant may be used to generate a current bone and implant model (e.g., via a front and a lateral x-ray). In another example, a 3D bone model may have been previously generated during implantation of the existing implant. The 3D bone model may be obtained and updated from the existing implant procedure.

In an example, a model of the bone comprises a surface geometry of parts of the bone that are exposed despite the presence of the implant or the limitations of the imaging. The model of the bone may include a surface geometry of the implant relative to adjacent bone surfaces, and a 3D geometry of the implant, for example using a 3D model of the implant (e.g., from the manufacturer, etc.).

The bone modeling may include generating a 3D surface of the bone when the bone modeling is not directly performed by the imaging equipment, or if not complete. In an example in which multiple implants are to be replaced (e.g., a total knee revision), all bones supporting implants may be modeled. Additional structures may be modeled as well, such as cartilage, hip joint, hip, ankle, etc.

In terms of planning, an operator may select a position or orientation of a 3D model of a replacement implant (e.g., a new implant) that is to be used in a revision surgery. In another example, the position or orientation may be automatically generated (e.g., using machine learning). Further planning may include determining a location for a cut plane to support the replacement implant. The planning may be assisted by an overlay of the revision implants on the bone models.

In an example, an intramedullary rod may be implanted to reinforce a bone. The planning may include determining a placement of an intramedullary rod (e.g., an orientation or position) using the robotic surgical device 102. For example, the robotic surgical device 102 may identify or may use a mechanical axis to place the rod or hollow out a canal for placement of the rod. In an example, the medullary cavity may be hollowed out by the robotic surgical device 102. Additional information including location or orientation of an intramedullary canal or an epicondylar axis may be used.

The 3D model of the bone with implant may comprise data pertaining to the surface geometry of a relevant portion of a bone and of the implant, including surfaces of the bone that are exposed despite the presence of the implant. The 3D model of the bone with implant may also include joint line information, full bone models with implants, mechanical axes, center of rotations, etc. The 3D models may also include a bone and revision implant planning model with an identification of implants that may be used, and bone alteration models to receive the implants and other accessories (intramedullary rods) based on surgical planning.

In an example, the robotic surgical device 102 may be used to cut the bone, for example using a reference guide developed from the 3D model of the bone and the existing implant. The robotic surgical device may autonomously perform the cut (e.g., using the optical navigation system 106 to guide the robotic surgical device 102). The optical navigation system 106 may track the optical navigation device 110, which may be affixed to a bone or an implant of the patient, or affixed to a portion of the robotic surgical device 102. Several optical navigation devices (e.g., trackers) may be used, for example one on each of a femur, tibia, the robotic surgical device 102, and an existing implant. From the tracking information gathered by the optical navigation system 106, used to track each of the optical navigation devices, the robotic surgical device 102 may be guided to perform a cut (e.g., to remove the existing implant).

After the existing implant has been removed (by the surgeon or by the robotic surgical device 102 autonomously or collaboratively as a force assist device), the robotic surgical device 102 may be used to reregister a surface of the bone or replan a new implant (e.g., modify a preoperative plan intraoperatively).

In an example, the computing device 104 may predictive what anatomy of the patient's bone looked like (e.g., before the existing implant degraded, before the existing implant was put in, or before the existing implant was needed, such as when the bone was health). From the predicted anatomy, a model may be generated or kinematic information may be determined.

An example technique using the robotic surgical device 102 may include performing a cut to remove an existing implant (e.g., using the robotic surgical device 102). The technique may include mapping an existing surface (e.g., an articular surface), and predicting the surface in a prior state. The robotic surgical device 102 may be used as a cut guide to perform a cut on the existing surface based on kinematic information of the predicted surface. In another example, the robotic surgical device 102 may perform the cut autonomously.

The robotic surgical robot 102 may be used to determine a level of constraint. For example, with a particular amount of laxity detected by the robotic surgical robot 102, a corresponding level of constraint may be used. The level of constraint may be determined based on how much constraint the component system provides due to the loss of ligament or patient anatomy (e.g., hinges are a high level of constraint, posterior stabilized may be a lower level of constraint).

The robotic surgical device 102 may be used to provide stability during a procedure. For example the robotic surgical device 102 may maintain control of a level of constraint (e.g., a particular amount of laxity may correspond to a particular level of constraint). The level of constraint may include how much constraint a component system provides due to the loss of ligament or patient anatomy (e.g., hinges are a high level of constraint).

The level of constraint may be selected by a surgeon, with suggestions displayed on a user interface. The suggested level of constraint may be displayed during a surgical procedure. For example, a next higher level of constraint may be suggested when detected laxity has reached or exceeds a particular level. In an example, when a basic poly or ultra-congruent is used, the robotic surgical device 102 may determine that laxity has reached a particular level and a user interface may display a suggested next-level of constraint. The correspondence of laxity level to constraint level may be based on a model or a set of features, used to determine when a next level of constraint is needed. The robotic surgical system 100 may output a warning alert, for example an audible or visible alert via the robotic surgical device 102 or a user interface of the computing system 104.

In an example, a surgeon places a trial in a patient knee at a particular level of constraint, and when robotic surgical device 102 detects a particular level of laxity, a warning alert may be output. The warning alert may indicate that the surgeon should increase the constraint (e.g., to a suggested next level). The laxity detection and constraint suggestion may be performed periodically, for example intraoperative throughout a procedure. The on-going detection throughout the procedure may be particularly useful when trials are placed, when implants are placed, or the like. The laxity may be continuously checked to suggest additional constraint (e.g., iteratively, for example a second higher constraint may be suggested after a first higher constraint is suggested and implemented or ignored). The laxity may be checked in a final knee evaluation, in an example.

Figure 2A:
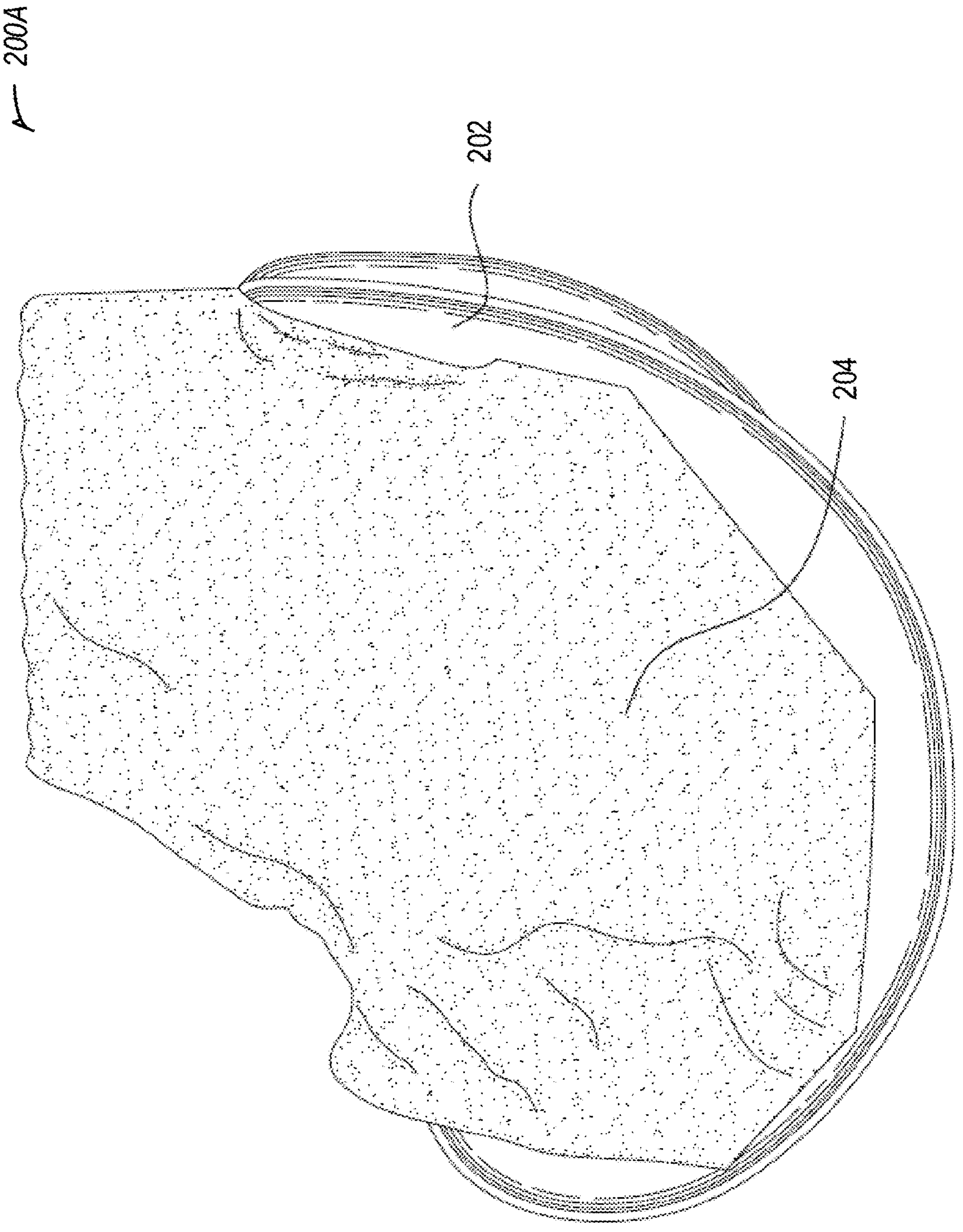
FIG. 2A illustrates a knee, including an implant, of a patient undergoing a revision in accordance with at least one example of this disclosure.

FIG. 2A illustrates a surgical field 200A, including an implant 202 affixed to a bone 204 of a knee of a patient undergoing a revision in accordance with at least one example of this disclosure. The surgical field 200A may include a model or an image of the patient. When the surgical field 200A includes a model, the model may be generated using imaging techniques, such as from two x-rays, for example a frontal and a lateral x-ray. These two x-rays may be lined up and a model may be generated using a 3D projection or estimation of the patient anatomy. Other imaging techniques may be used, such as CT scanning (computerized tomography), fluoroscopy, or like radiography methods, for example any that provide suitable resolution of images.

In an example, the patient anatomy may be modeled preoperatively, and used to plan steps of a revision surgical procedure. Deviations from the plan may occur during the procedure, and modifications to the plan (e.g., replanning) may occur intraoperatively, particularly when using a robotic surgical device (e.g., as described above with respect to element 102 of FIG. 1).

In another example, FIG. 2A may include a model generated intraoperatively, for example using registration and optical navigation. This model may not be a fully rendered 2D or 3D model of the patient anatomy, but may instead include key points, interpolated or extrapolated points, or other information used for completing a revision procedure.

The models described with respect to the patient anatomy need not be actually rendered or displayed. Instead, the models may be used by a robotic surgical device to perform portions of a revision procedure. For example, coordinates of registered points and interpolated or extrapolated other points, simulation of coordinates as moved or cut during a procedure, or the like may be stored in memory. A robotic surgical device may retrieve data stored in the memory when performing a portion of the revision procedure.

Figure 2B:
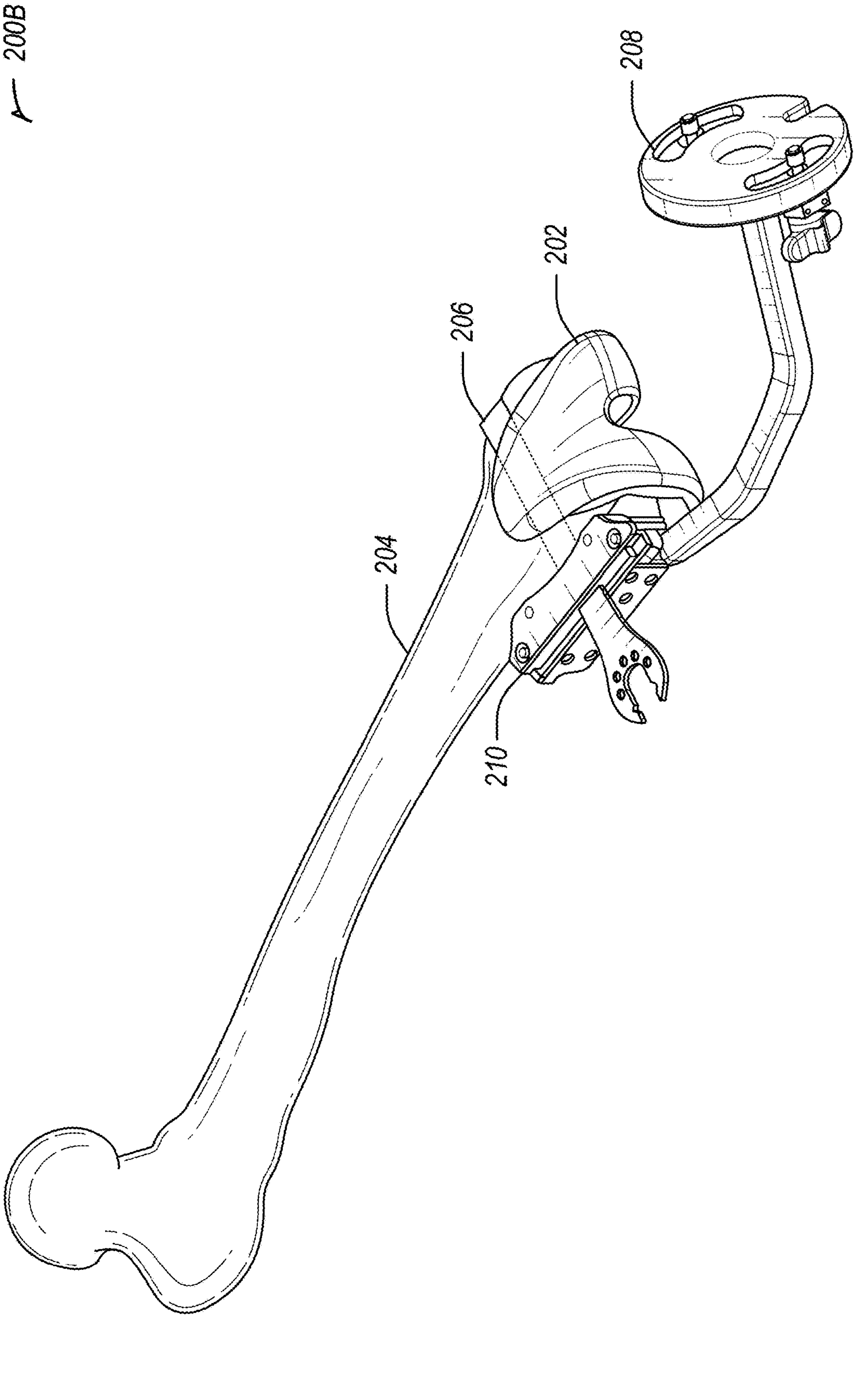
FIGS. 2B-2C illustrate implant removal systems using a robotic arm in accordance with at least one example of this disclosure.

FIG. 2B illustrates an implant removal system using a robotic arm 208 in accordance with at least one example of this disclosure. FIG. 2B illustrates a diagram 200B of patient anatomy (e.g., bone 204 with an implant 202 affixed to the bone 204) with the robotic arm 208 (end effector shown, but understood to be connected or coupled to a robotic arm), optionally as a model, or as a patient within a surgical field. The robotic arm 208 may be used to position a cut guide 210 to allow a cut to be made by a cutting instrument 206, for example, under the implant 202. The cut may be part of a revision procedure, for example to remove the implant 202 before replacing the implant 202 with a new implant.

In an example, the diagram 200B is a model that includes an image of the knee as it is imaged (e.g., with an existing implant, and potentially damaged). A technique may be used to modify the model, for example by simulating cuts to be made (e.g., by a robotic surgical device) to remove the existing implant. Other modifications may include simulating a new implant after the existing implant is removed, preparing the bone 204 for receiving the new implant, or the like. In an example, the implant 202 is an existing implant. In another example, such as after simulation, the implant 202 may be a new implant. The bone 204 may represent the existing bone, or similarly, after simulation, may include modified bone (e.g., prepared for the new implant or after removing the existing implant).

The diagram 200B may be used as a model for planning cuts during an implant removal step of a patent application for robotic knee revision. The rendering shows the cut guide 210 being used (after navigation by the robotic arm 208) to guide a cutting instrument 206 to perform a cut between the bone 204 and the implant 202 for implant removal. In an example, the diagram 200B may show a live version of patient anatomy, a modeled version, or the like.

The model may be based on captured images (e.g., an x-ray, CT, MR, etc.). The model may indicate various aspects of the patient anatomy and other aspects of the surgical field represented in the diagram 200B. For example, based on modeling (e.g., using machine learning, binary classification, or the like), the bone 204 may be highlighted in the model in a first manner (e.g., a color, a transparency, etc.) and cement attached to the bone 204 or the implant 202 may be highlighted in the model in a second manner. The pre-operative imaging may indicate what is bone and what is cement, for example based on color, density, etc., in the medical image. The implant 202 may be highlighted in a third manner, in an example. A pre-operative plan created using the model may include consideration of the areas that are cement, to guide a surgeon to remove the cement. Cement is radio-opaque, so it may be identified using an x-ray.

Other details of the patient anatomy and instruments may be highlighted or identified in the diagram 200B. For example, details about the implant 202 may be identified. These details may include a size of the implant, a type of the implant, a manufacturer of the implant, a placement or location of the implant relative to patient anatomy, or the like. An image of the implant 202, captured via an x-ray or other medical imaging, for example, may be compared to stored images of implants to determine a size, type, or manufacturer of the implant 202. In another example, a size of the implant 202 may be determined based on a known size of the bone 204. The determined size of the implant may include an estimate. The size may include an anterior-posterior size, an anterior-posterior box dimension, or medial-lateral width, in an example. In some examples, the manufacturer of the implant 202 may be identified based on identifying marks or words on the implant (e.g., an engraving), via a particular style or shape, or the like.

In another example, diagram 200B illustrates a robotically assisted revision surgery to remove a worn-out implant (e.g., implant 202). In this example, the planning performed as discussed above is implemented on a robotic surgical system to position cut guide 210 in various positions to guide removal of the implant 202 using cutting instrument 206. In an example, the cutting instrument 206 is a surgical saw (only the blade is illustrated for clarity) guided by the robotically controlled cut guide. As discussed above, the pre-operative plan can determine locations for the cut guide 210 to be positioned relative to the implant 202 and bone 204 to allow for optimal removal of the implant 202 with minimal bone loss. Further, robotic positioning of the cut guide 210 can assist in ensuring that the cuts align with pre-operative plans, which in turn allows for greater precision in placement of revision implants.

In an example, the cutting instrument 206 may include a include a pencil-tip style burr. In this example, the cutting instrument 206 may be without the cut guide 210 (e.g., in cases where the cut guide 210 may not fit in an anatomic area during surgery). The pencil-tip style burr may be controlled by the robotic arm 208 instead of holding the cut guide 210, in this example.

Figure 2C:
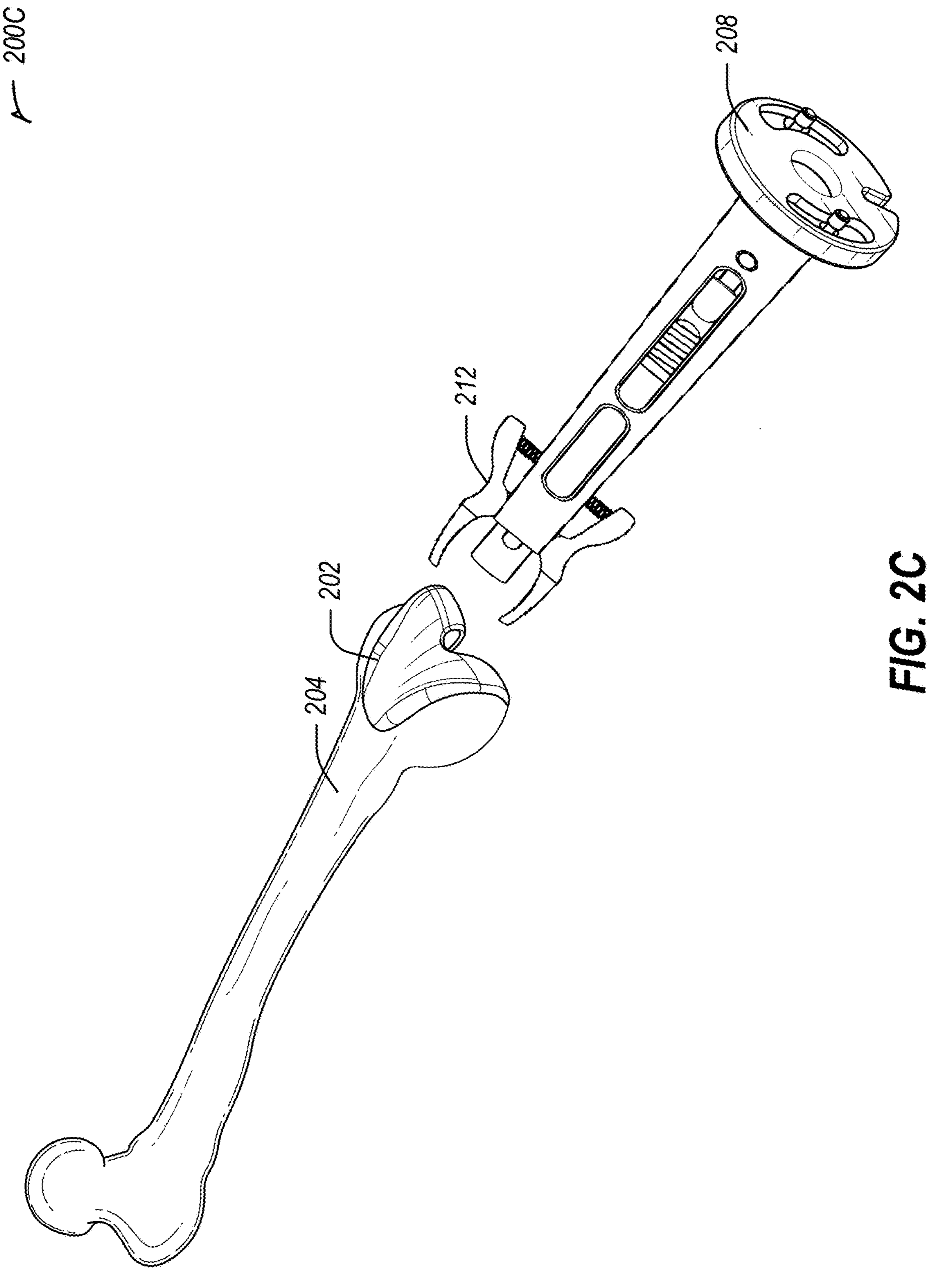

FIG. 2C illustrates an implant removal system 200C using a robotic arm 208 in accordance with at least one example of this disclosure. The system 200C uses a removal device 212 attached to an end effector of the robotic arm 208 to remove an implant 202 from a bone 204. The removal device 212 may be configured to attach to or secured around the implant 202. The robotic arm 208 may apply a force, for example a force along an axis of the bone 204.

The robotic arm 208 may create a force to remove the implant 202 from the bone 204. In an example, the force may be applied directly in line with a canal of the bone 204. In an example, the robotic arm 208 may be used to constrain the direction of the impaction. In this example, the force may be applied by the robotic arm 208 or by a surgeon (e.g., with a mallet or other device), while the robotic arm 208 maintains the direction of the force. The removal device 212 may include gripper arms, which may be manipulated using a linkage to adjust the distance between the gripper arms to grip the implant 202. For example, the gripper arms may be biased to grasp the implant 202. Although FIG. 2C illustrates this technique with a femoral implant 202, a tibial implant or other orthopedic implant may be removed using this technique.

Figure 3A:
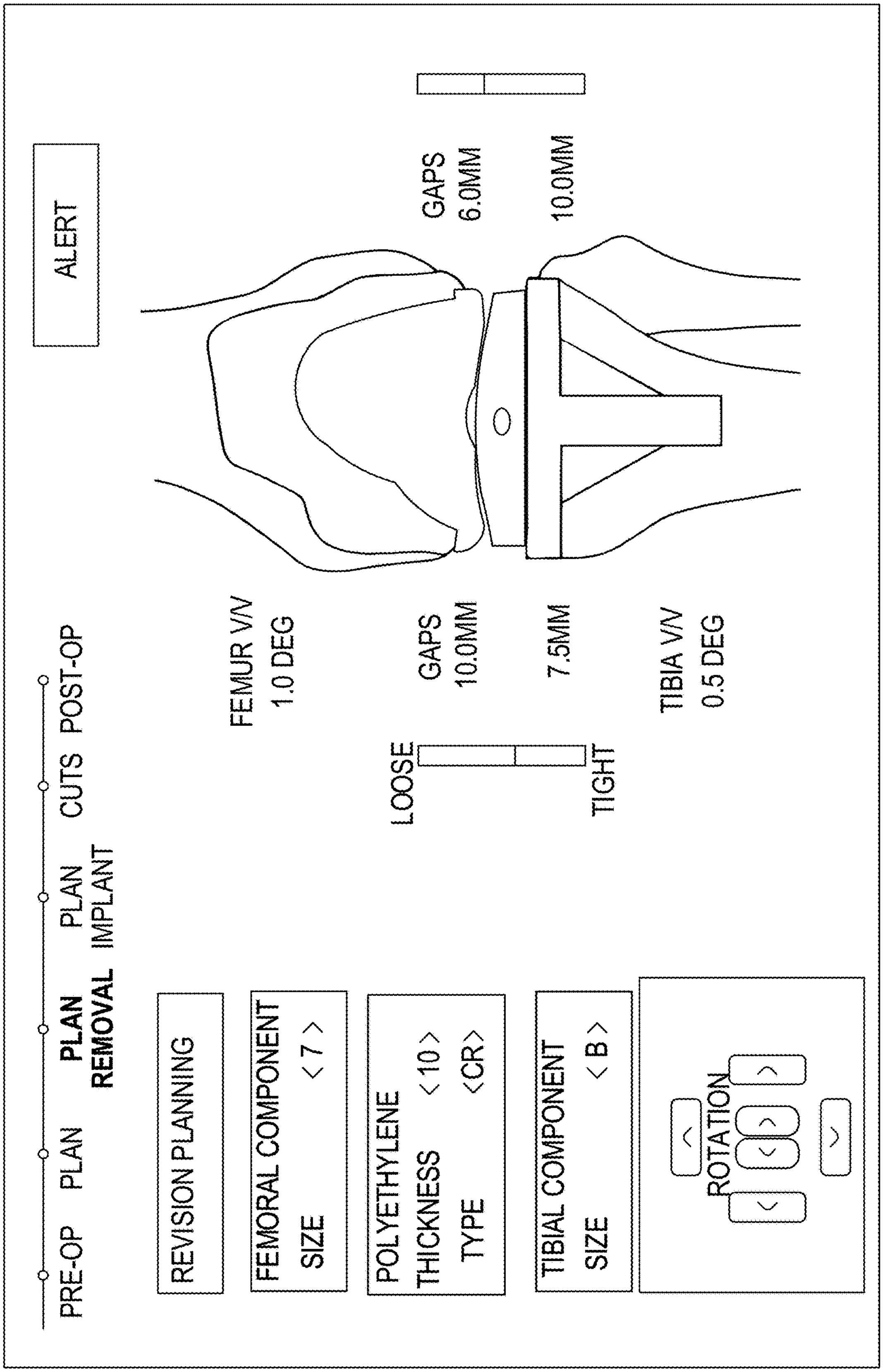
FIG. 3A illustrates a user interface for planning aspects of a revision (e.g., a cut or a new implant) in accordance with at least one example of this disclosure.

FIG. 3A illustrates a user interface 300A for planning aspects of a revision (e.g., a cut or a new implant) in accordance with at least one example of this disclosure. For example, the user interface 300 may be used for removal planning, new implant planning, control of a robotic surgical device, control of system components, or the like.

Figure 3B:
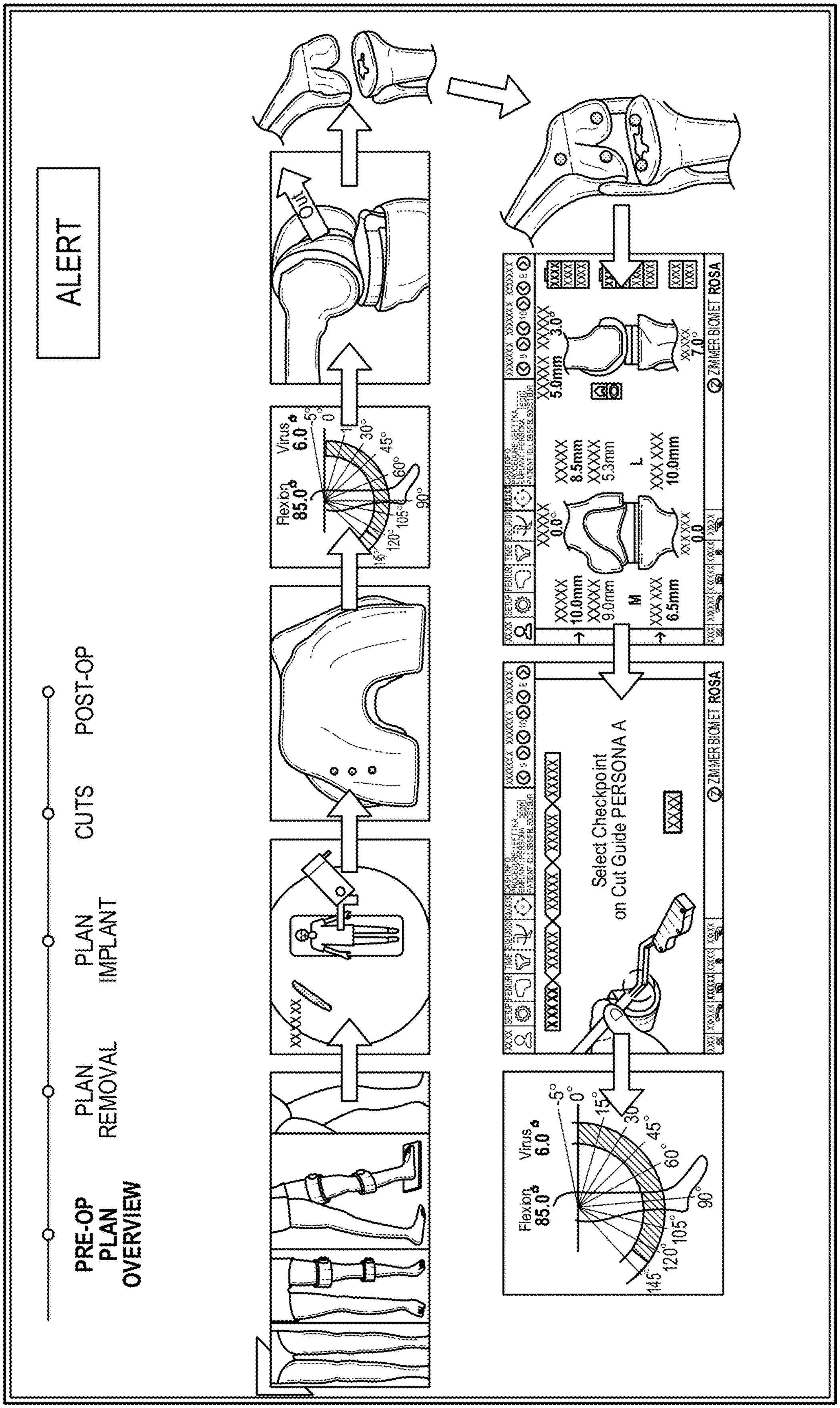
FIG. 3B illustrates a user interface including a pre-operative plan in accordance with at least one example of this disclosure.

FIG. 3B illustrates a user interface 300B including a pre-operative plan in accordance with at least one example of this disclosure. The planning shows a series of images as an example of what a pre-operative plan may look, and how a surgeon may proceed through a revision surgery. The plan shows medical imaging, positioning, implant identification and orientation with optional landmarks on the implant, identification of cement and bone, range of motion information including degree of flexion or extension with varus or valgus angles or laxity, identification of implant removal, bone example with the implant removed, identification of anatomical markers, new implant planning details (e.g., intraoperative planning, including a joint line, gap balancing, alignment, or the like), a cut guide user interface, and a final range of motion testing user interface. During pre-operative planning, existing hardware (e.g., an implant) may be identified and displayed on the user interface 300B. The planning software may propose a stem length for a tibial implant, in an example. The stem length may be determined based on medical imaging of patient anatomy prior to the pre-operative planning.

In an example, the pre-operative planning may include consideration of a patient's fibular head (e.g., a proximal portion of the fibula). The fibular head maybe used to orient the tibia or femur in imaging, estimate an amount of tibia remaining, or other aspects based on a fibula landmark. A fibula landmark may be displayed on user interface 300B for further evaluation.

Figure 4:
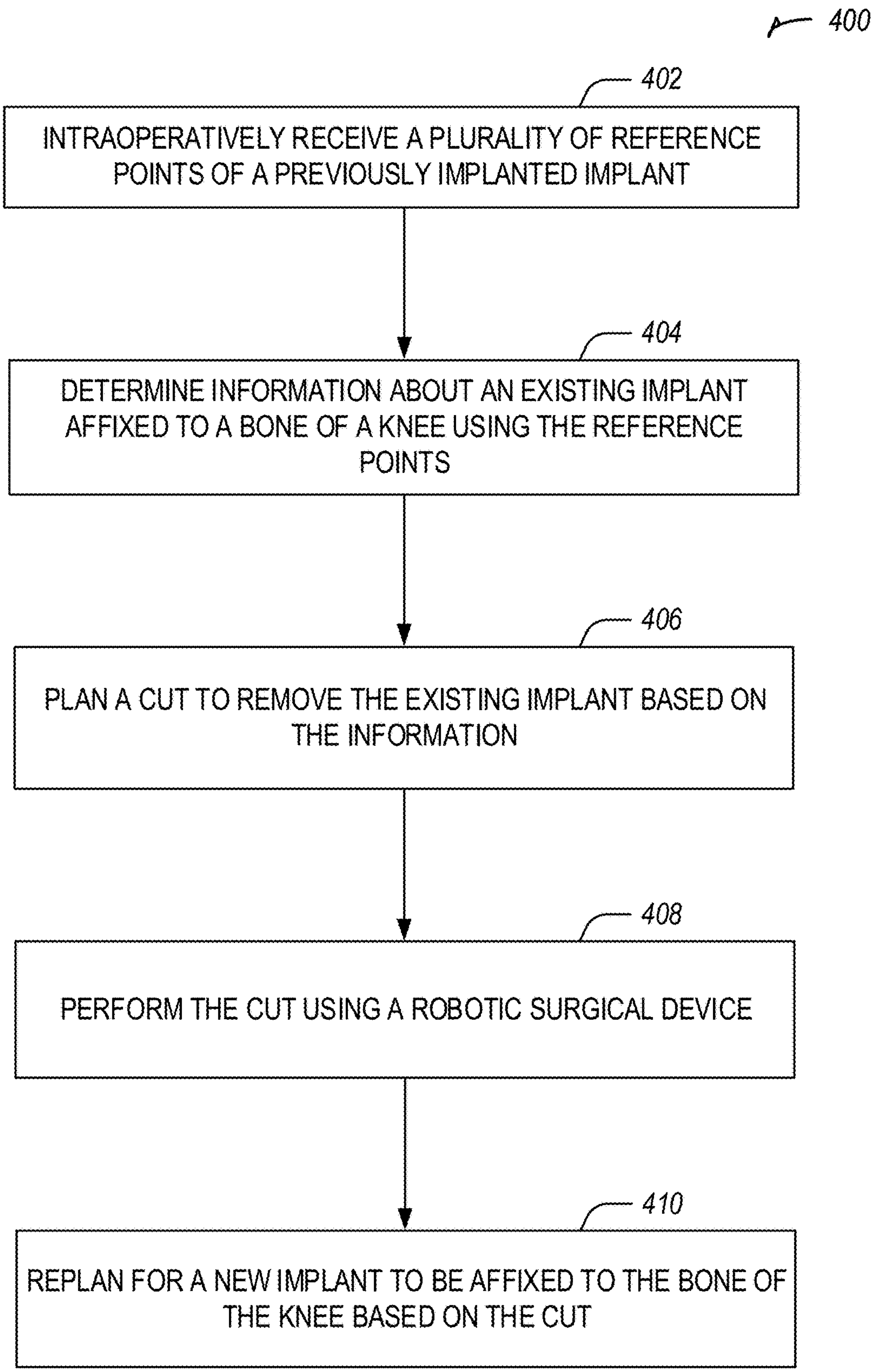
FIG. 4 illustrates a flowchart showing a technique for performing a robotic revision knee arthroplasty in accordance with at least one example of this disclosure.

FIG. 4 illustrates a flowchart illustrating a technique 400 for performing a robotic revision knee arthroplasty in accordance with some embodiments. The technique 400 includes an operation 402 to intraoperatively receive a plurality of reference points of a previously implanted implant. Operation 402 may include capturing an x-ray and generating the reference points from identifiable portions of the x-ray. In an example, operation 402 includes registering the plurality of reference points on the existing implant intraoperatively.

The technique 400 includes an operation 404 to determine information about an existing implant affixed to a bone of a knee using the reference points. The information about the existing implant may include at least one of an implant type, a maker of the implant, degradation information about the implant, a failure reason for the implant, or the like. The technique 400 includes an operation 406 to plan a cut to remove the existing implant based on the information. In an example, operation 406 includes predicting a surface for the new implant.

The technique 400 includes an operation 408 to perform the cut using a robotic surgical device. Operation 408 may include using the robotic surgical device as a robotic guide. In another example, operation 408 may include using the robotic surgical device to perform the cut automatically. In an example, operation 408 includes cutting under the existing implant using the robotic surgical device. In this example, cutting under the existing implant means cutting a portion of bone and the implant away from the remaining portion of the bone. In another example, operation 408 includes contouring or performing a fine cut or burr to create a flat surface on the bone or to prepare a canal for a stem using the robotic surgical device.

The technique 400 includes an operation 410 to replan for a new implant to be affixed to the bone of the knee based on the cut. In an example, operation 410 includes using predictive analytics or a bone atlas to replan for the new implant. The technique 400 may include an operation to install the new implant, for example using the robotic surgical device as a guide, using the robotic surgical device to move the implant, using the robotic surgical device as a force-assist device, or the like.

The technique 400 may include an operation to use optical navigation to register the reference points. The technique 400 may include an operation to robotically prepare a canal for the new implant. The technique 400 may include an operation to plan a clean-up cut after the (initial) cut is performed.

Figure 5:
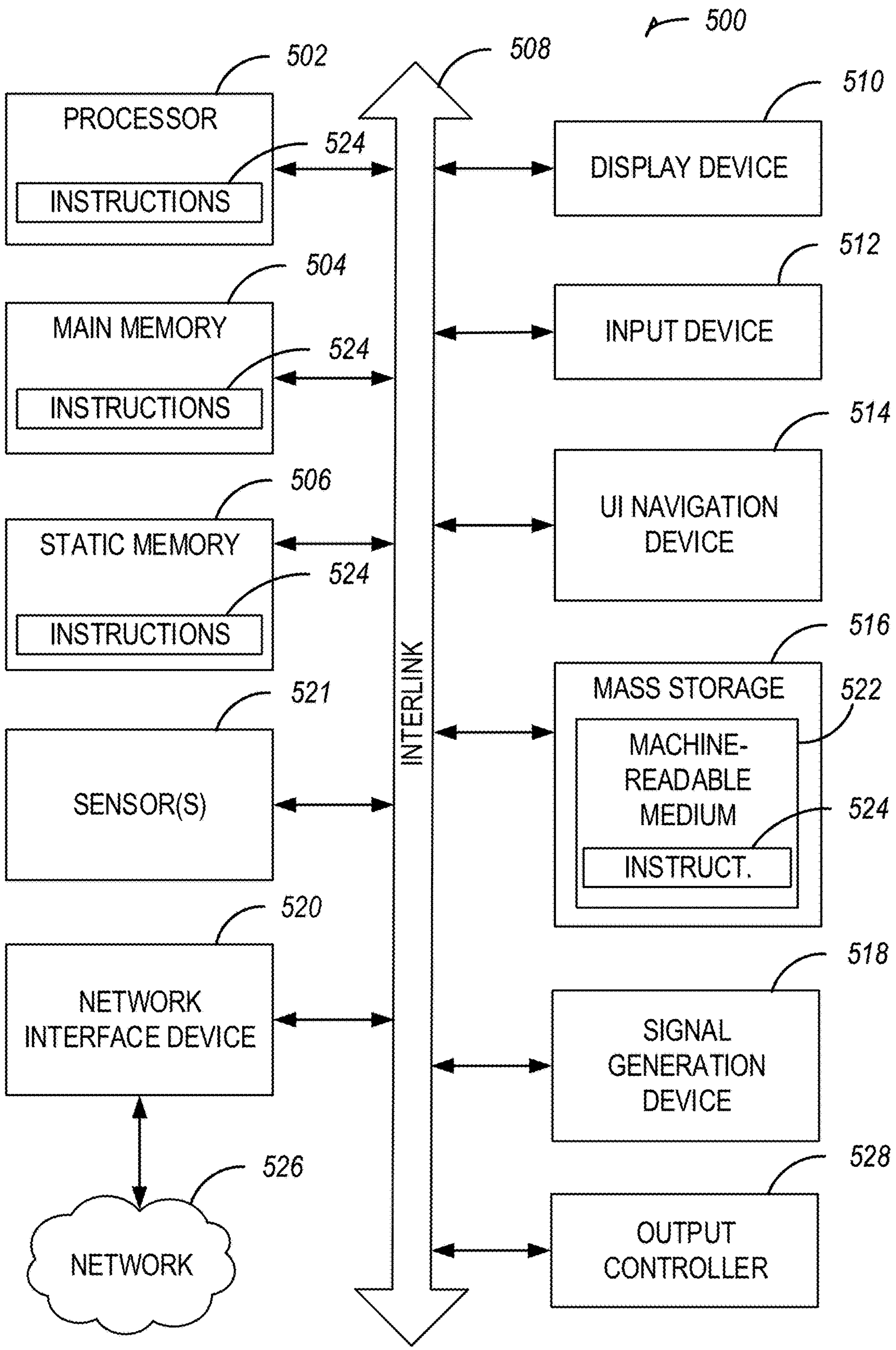
FIG. 5 illustrates a block diagram of an example machine upon which any one or more of the techniques discussed herein may perform in accordance with at least one example of this disclosure.

FIG. 5 illustrates a block diagram of an example machine 500 upon which any one or more of the techniques discussed herein may perform in accordance with some embodiments. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524. The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Figure 6:
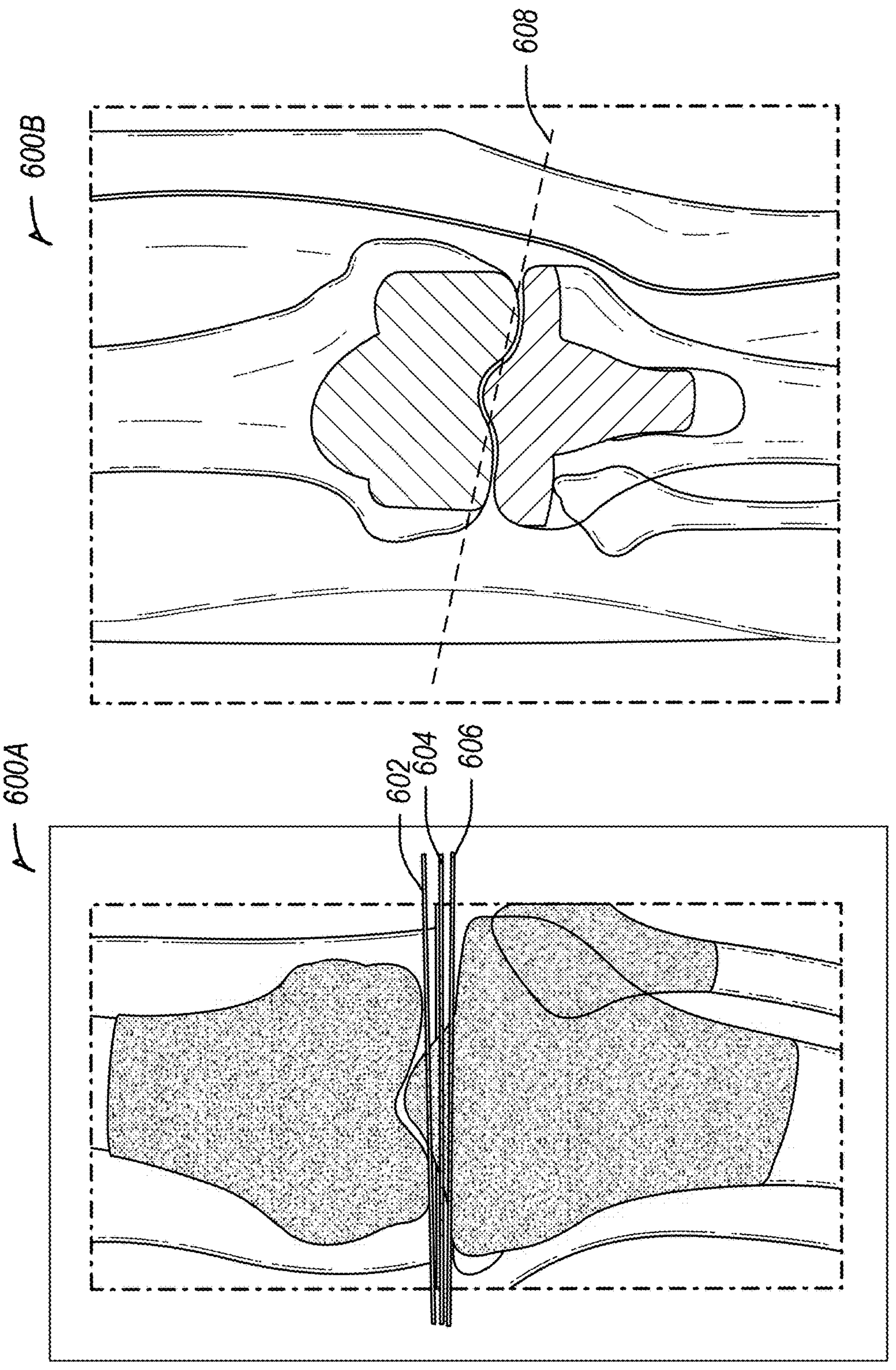
FIG. 6 illustrate examples of a joint line on a model of patient anatomy in accordance with at least one example of this disclosure.

FIG. 6 illustrate example views 600A and 600B of a joint line on a model of patient anatomy in accordance with at least one example of this disclosure. A plurality of joint lines 602, 604, and 606 are shown in example 600A, while a single joint line 608 is shown in example 600B. In some examples, example 600A is a first view and example 600B is a second view of the same patient anatomy.

A joint line is a reference line relative to aspects of knee anatomy of a patient (e.g., a mechanical axis, a kinematic axis, an axial line of a bone, such as the femur or tibia, landmarks of the femur or tibia, etc.). The joint lines (e.g., 602, 604, 606, or 608) displayed may indicate estimations of the joint line to be used for a revision procedure on a knee represented in the example views 600A or 600B.

In an example, a robotic surgical device may be used to during a revision. For example, the robotic surgical device may provide stability to a bone or implant during a portion of the procedure. In an example, the robotic surgical device may collect data (e.g., sensor data). In an example, the robotic surgical device may be used with optical navigation to perform a burr during the techniques described herein. The robotic surgical device may be used to hold a cut guide for performing a cut (e.g., to remove bone or an existing implant). In some examples, a robotic surgical device may be used to register aspects of a bone or implant, such as with the existing implant in (e.g., intraoperatively) or after the existing implant is removed. The robotic surgical device may be used to provide assistance with cuts. The robotic surgical device may provide a reference to a joint line (e.g., having a degree of varus or valgus), provide a recreation of a joint line (e.g. using modeling techniques), provide predictive analytics of a projected joint line (e.g., based on previous implant, new implant, or probability prediction), or the like. Recreation of joint line or other bone recreation may include identification of joint line parameters by using a digital implant 3D model as overlaid onto the image of bone and implant.

The robotic surgical device may collect data, such as the joint line information described above or a thickness of revision. The robotic surgical device may allow for intra-operative adjustments, replanning, or additional precision (e.g., to leave more bone in the patient and less cut off than in traditional techniques).

In an example, a single joint line may be displayed (e.g., a joint line with a highest probability estimated using robotic measurements of landmarks), or multiple joint lines (e.g., with small variations) may be displayed for a surgeon's selection. The joint line or lines may be determined by extrapolating from available landmarks or using robotic sensing. Typical landmarks to identify a joint line pre-operatively may not exist or may not be identifiable in a revision procedure (e.g., due to previously cuts, obscured by an existing implant, bone deterioration, or the like). In an example, an epicondyle landmark may be used in a revision procedure to identify a joint line.

The joint line or lines may be estimated using an artificial intelligence procedure (e.g., a machine learning model), for example based on shape matching to determine healthy bone of a reference model. The joint lines estimated using this procedure may not be precise, and thus multiple joint lines may be displayed for a surgeon to select. A comparison of existing patient anatomy (e.g., femur or tibia, with or without implant) may be made to an atlas of x-ray data, in an example, to identify a likely joint line or lines.

In another example, a contra-lateral joint line may be determined (e.g., when a patient has one knee that does not have an implant, and another knee being planned for a revision having an implant). The joint line on the other knee (e.g., assuming there is no implant) may be used to estimate a joint line on the knee to undergo the revision.

In yet another example, landmark features may be used that are not typically used in generation of joint lines. These landmark features may be difficult for a person to identify. These landmark features may be identified by an AI model using labeled atlas images. In some examples, bone may be extrapolated (e.g., revealing landmarks that are more easily correlated to the joint line). In other examples, an AI model may use what is left of the tibia or the femur to determine the joint line based on remaining landmarks. Either technique may include generating a model of the bone or bones, and comparing the bone or bones to atlas bones to extract a model of the bones or the joint line. In some examples, where an implant may be identified (e.g., a size, a brand, a type, etc. of the implant), then that information may be used as calibration or for navigation to determine where landmarks would be in healthy bone, and thus determine a joint line.

The different joint lines 602, 604, 606 on example 600A may be selectable by a surgeon (e.g., displayed on a user interface) such that the surgeon may choose one for planning a revision procedure. Once selected, the joint line may be modified later, for example to select a different joint line or move the joint line manually. The different joint lines 602, 604, 606 may be identified using one technique, with different estimations based on a range of tolerance, in one example. For example, a median or average estimate may be identified and displayed as joint line 604. An error range may be identified for the median or average estimate, and joint lines 602 and 606 may be displayed based on the error range (e.g., at 25% and 75% of the error range, half way from the median or average estimate to an extreme of the error range, or at limits of the error range). Additional joint lines may be displayed as well, the display is not limited to three joint lines.

In another example, two joint lines (e.g., any two of 602, 604, and 606) may be generated using different techniques. For example, one of the joint lines may be determined by extrapolating bone using a comparison to a bone or bones an atlas, and determining a joint line from a closest extrapolation or a set of close bone extrapolations (which may include using a closest model directly, or extrapolating between or among models, which may include an extrapolation not directly represented in the atlas). Another technique may include using landmarks (e.g., using a robotic surgical device to determine difficult or non-typical landmarks, or extrapolating estimated landmarks from current data). Still another technique may include using a model (e.g., a machine learning or other AI model), based on previous data (e.g., a supervised learning technique model) to identify the joint lines. Joint line 608 may represent an average or median of multiple techniques.

Figure 7:
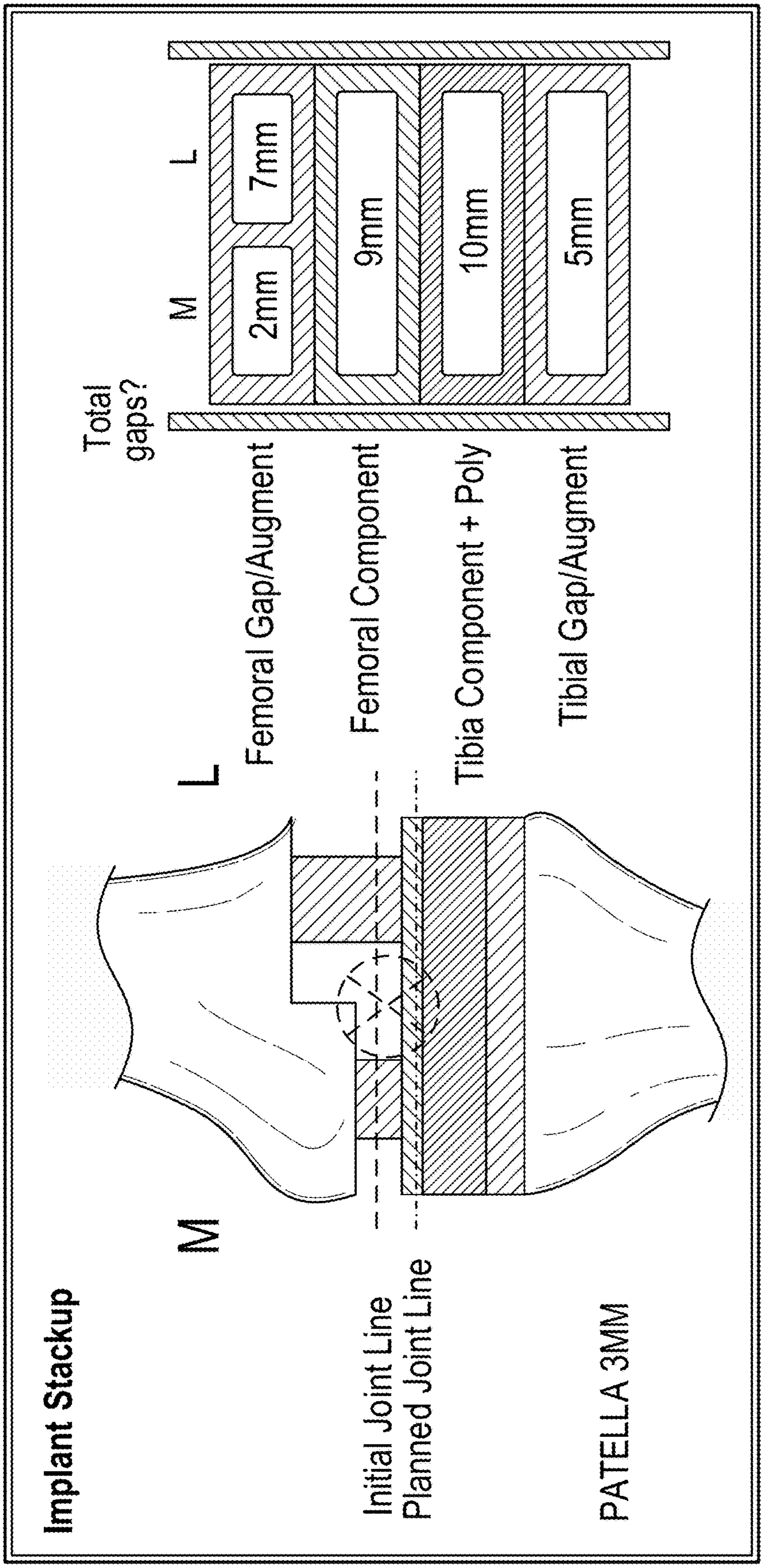
FIG. 7 illustrates a wedge augmentation planning user interface in accordance with at least one example of this disclosure.

FIG. 7 illustrates a wedge augmentation planning user interface 700 in accordance with at least one example of this disclosure. Once a joint line is identified or selected, regardless of by which technique or techniques, the joint line may be used to plan a cut, an implant, or the like. For example, gap or alignment planning may use the joint line to determine whether a wedge is needed, and if so, what size wedge. For example, as shown in the planning user interface 700, an example of a medial gap of two millimeters and a lateral gap of seven millimeters may be planned. A wedge on the lateral side of five millimeters may be used or suggested for use to achieve the gap balancing or offset. The sizes (e.g., the two, five, or seven millimeters) may be distances from the joint line to patient anatomy (e.g., femur).

In an example, the planning user interface 700 may be used in placing, modifying, or removing a wedge augmentation implanted to compensate for tibial bone deficiency. A wedge or other augment (wedge is used herein for convenience, but any kind of augment may be substituted) may be selected. The selection maybe based on shape or thickness of the wedge, as well as the needed augment size. The wedge selected may be automatically suggested based on information about patient anatomy (e.g., measurements from medical imaging), or input manually.

In an example, the planning user interface 700 may be used intraoperatively. For example, an existing component may be removed, registration may be taken of various points or landmarks on the patient anatomy (e.g., femur or tibia), and remaining surfaces may be mapped and displayed. The augment may be placed in the user interface 700 for testing, comparison, or visualization. The intraoperative planning may include a bone loss assessment, where, after removing the implant and optionally after clean-up cuts, remaining bone may be digitize. The needed augments may be estimated based on the digitized bone, for example using an AI model, or based on comparisons to previous augment situations. What augment is needed may be recommended on the planning user interface 700.

Figure 8A:
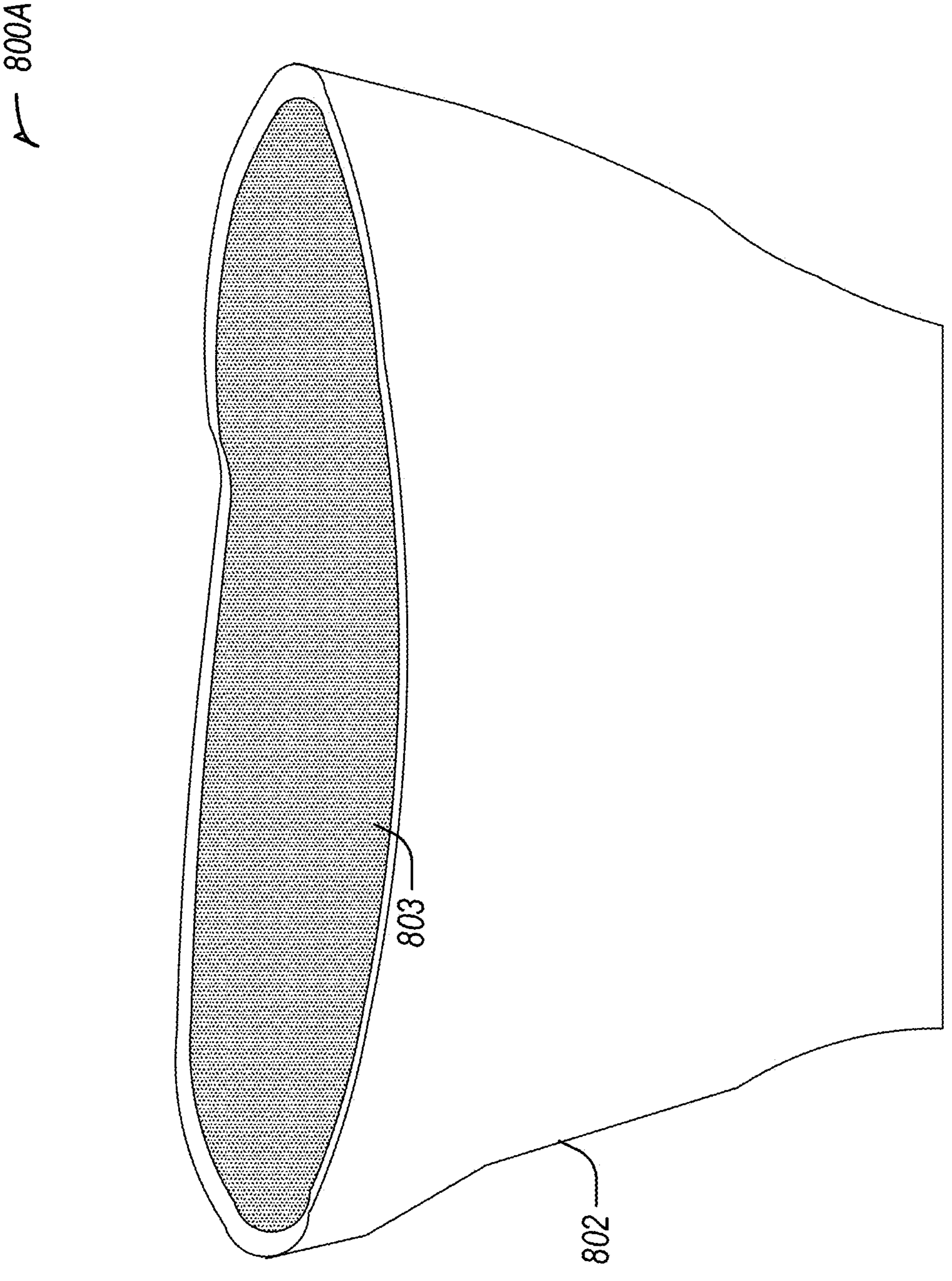
FIGS. 8A-8B illustrate diagrams including a tibia for preparing for revision in accordance with at least one example of this disclosure.
Figure 8B:
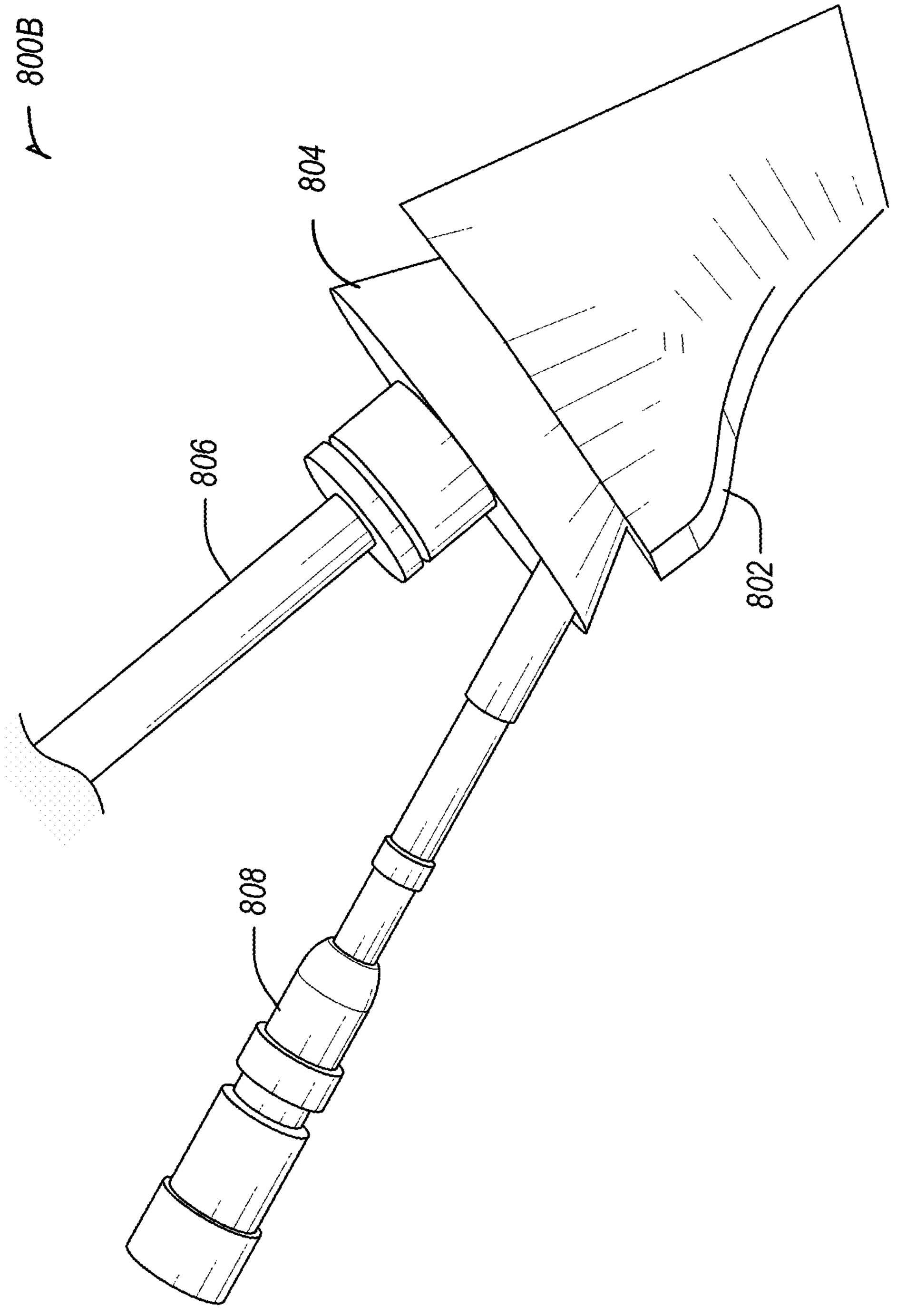

FIGS. 8A-8B illustrate diagrams including a tibia for preparing for revision in accordance with at least one example of this disclosure. FIG. 8A illustrates a diagram 800A including a tibia 802 with a surface 803 to be prepared for a tibial stem. In an example, a burring technique may be used to flatten the tibial surface 803.

FIG. 8B illustrates a diagram 800B including a cone 804 for securing a tibial stem 806 in the tibia 802, in accordance with at least one example of this disclosure. The stem 806 is typically used in a knee revision procedure to stabilize the knee joint by transferring forces and stresses. However, the stem 806 may not be sufficiently able to be placed due to bone loss, issues. Thus, the cone 804 is used to stabilize the stem 806 within the tibia 802. Aspects of the diagram 800 may be represented by a visualization on a user interface, where different cones or stems may be tried pre- or intra-operatively before placing the actual cone 804 or stem 806. A placement instrument 808 may be used to assist in placing the stem 806 or cone 804. In an example, the placement instrument 808 may be controlled by a robotic arm.

In an example technique, a surgical robot may be used for contouring or finer cuts, or a burr to act on a smaller volume to create a flat surface (e.g., on surface 803). These cuts or burrs may be used to refine a surface of the bone. For example, the burr may be used to prepare the tibia 802 for the cone 804 and stem 806. The burring may be performed by a robotic surgical system automatically, for example by using imaging or live camera of the tibia 802. A target surface may be planned (pre-operatively or intra-operatively) for the tibia 802, which may be burred on the surface 803 using a robotic arm. The plan may indicate locations to burr, a depth to burr, or a surface layout, which the robotic arm may perform automatically. In another example, the robotic arm may burr the surface 803 of the tibia 802 cooperatively with the surgeon, for example in a force-assist (robotic arm amplifies surgeon force) or force-resist (robotic arm resists forces applied by surgeon that are not safe or within a plan) set-up.

Although FIGS. 8A-8B discuss tibial cones (e.g., tibial cone 804), a similar procedure may be used for a femoral cone. For example, burring or small cuts may be performed by or with a robotic arm before placing a femoral cone for use in securing a femoral stem or other device.

Figure 9:
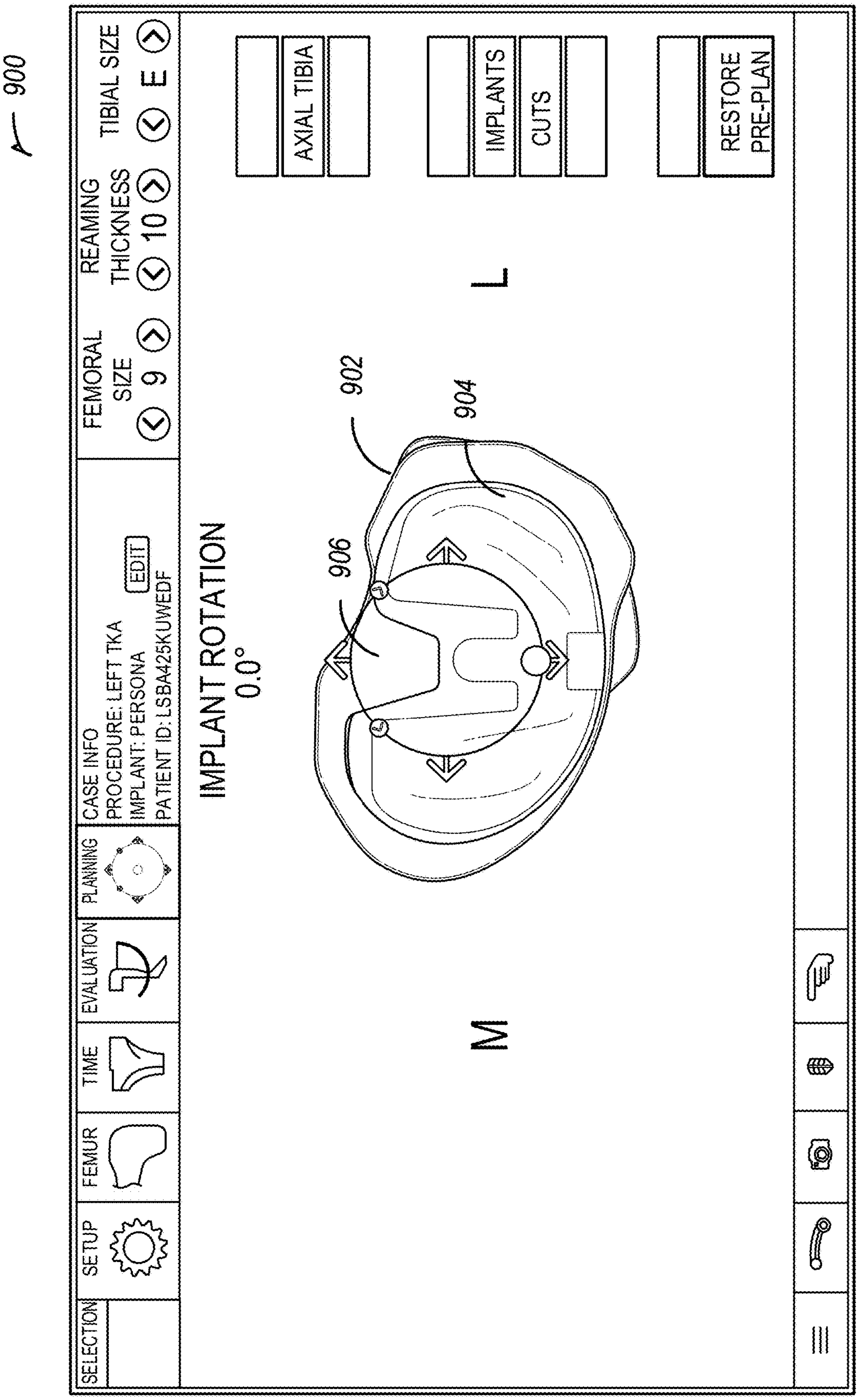
FIG. 9 illustrates a tibial stem planning user interface in accordance with at least one example of this disclosure.

FIG. 9 illustrates a tibial stem planning user interface 900 in accordance with at least one example of this disclosure. The user interface 900 illustrates a tibia 902 including a tibial implant 904 (e.g., a stem), and a rotational positioning interface component 906. The rotational positioning interface component 906 may be used to virtually move the tibial implant 904 (e.g., rotate the tibial implant 904, or translate it) on the planning user interface 900. The tibia 902 may be a model based on patient anatomy (e.g., from medical imaging).

The tibial implant 904 may include a stem offset on the rotation, which may be changed by a surgeon. For example, different offsets of 0, 3, or 6 millimeters may correspond with three different stems. Further visualization of the tibial implant 904 may be displayed at different rotational positions (e.g., 24 rotational positions of each stem).

A surgeon may place the tibial implant 904 in a desired position, and then the planning assist software may output the stem offset and the angle, in one example. In another example, the surgeon may navigate the tibial implant 904 itself on the tibia 902 (on the planning user interface 900), and an AI (e.g., a model) may generate the offset and angle from a live camera view. In still another example, the surgeon may specify offset and angle, and the planning user interface 900 may automatically place the tibial implant 904 in a corresponding position for surgeon review.

Each of the following non-limiting examples may stand on its own, or may be combined in various permutations or combinations with one or more of the other examples.

Example 1 is a method of performing a robotic revision knee arthroplasty, the method comprising: intraoperatively receiving a plurality of reference points of a previously implanted implant; determining information about an existing implant affixed to a bone of a knee using the reference points; using a processor, planning a cut to remove the existing implant based on the information; performing the cut using a robotic surgical device; and replanning for a new implant to be affixed to the bone of the knee based on the cut.

In Example 2, the subject matter of Example 1 includes, installing the new implant.

In Example 3, the subject matter of Examples 1-2 includes, using optical navigation to register the reference points.

In Example 4, the subject matter of Examples 1-3 includes, robotically preparing a canal for the new implant.

In Example 5, the subject matter of Examples 1-4 includes, wherein receiving the plurality of reference points includes capturing an x-ray and generating the reference points from identifiable portions of the x-ray.

In Example 6, the subject matter of Examples 1-5 includes, wherein receiving the plurality of reference points includes registering the plurality of reference points on the existing implant intraoperatively.

In Example 7, the subject matter of Examples 1-6 includes, wherein the information about the existing implant includes at least one of an implant type, a maker of the implant, degradation information about the implant, or a failure reason for the implant.

In Example 8, the subject matter of Examples 1-7 includes, wherein planning the cut includes predicting a surface for the new implant.

In Example 9, the subject matter of Examples 1-8 includes, wherein performing the cut includes using the robotic surgical device as a robotic cut guide.

In Example 10, the subject matter of Examples 1-9 includes, wherein performing the cut includes using the robotic surgical device to perform the cut automatically.

In Example 11, the subject matter of Examples 1-10 includes, wherein replanning for the new implant includes using predictive analytics or a bone atlas.

In Example 12, the subject matter of Examples 1-11 includes, planning a clean-up cut after the cut is performed.

In Example 13, the subject matter of Examples 1-12 includes, wherein performing the cut using the robotic surgical device includes cutting under the existing implant using the robotic surgical device.

In Example 14, the subject matter of Examples 1-13 includes, wherein performing the cut using the robotic surgical device includes contouring or performing a fine cut or burr to create a flat surface on the bone or to prepare a canal for a stem using the robotic surgical device.

Example 15 is at least one machine-readable medium including instructions for performing a robotic revision knee arthroplasty, which when executed by a processor, cause the processor to: intraoperatively receive a plurality of reference points of a previously implanted implant; determine information about an existing implant using the reference points; plan a cut to remove the existing implant based on the information; perform the cut using a robotic surgical device; and replan for a new implant based on the cut.

In Example 16, the subject matter of Example 15 includes, wherein the instructions further cause the processor to cause the robotic surgical device to install the new implant.

In Example 17, the subject matter of Examples 15-16 includes, wherein the instructions further cause the processor to receive the reference points from an optical navigation device.

In Example 18, the subject matter of Examples 15-17 includes, wherein the instructions further cause the processor to cause the robotic surgical device to prepare a canal for the new implant.

In Example 19, the subject matter of Examples 15-18 includes, wherein to receive the plurality of reference points, the processor is further to generate the reference points from identifiable portions of an x-ray.

In Example 20, the subject matter of Examples 15-19 includes, wherein to receive the plurality of reference points, the processor is further to receive the plurality of reference points via registering the plurality of reference points on the existing implant intraoperatively.

In Example 21, the subject matter of Examples 15-20 includes, wherein the information about the existing implant includes at least one of an implant type, a maker of the implant, degradation information about the implant, or a failure reason for the implant.

In Example 22, the subject matter of Examples 15-21 includes, wherein to plan the cut, the processor is further to predict a surface for the new implant.

In Example 23, the subject matter of Examples 15-22 includes, wherein to perform the cut, the processor is further to configure the robotic surgical device as a robotic cut guide.

In Example 24, the subject matter of Examples 15-23 includes, wherein to perform the cut, the processor is further to cause the robotic surgical device to perform the cut automatically.

In Example 25, the subject matter of Examples 15-24 includes, wherein to replan for the new implant, the processor is further to use predictive analytics or a bone atlas.

In Example 26, the subject matter of Examples 15-25 includes, wherein the instructions further cause the processor to plan a clean-up cut after the cut is performed.

In Example 27, the subject matter of Examples 15-26 includes, wherein to perform the cut using the robotic surgical device, the processor is further to cut under the existing implant using the robotic surgical device.

In Example 28, the subject matter of Examples 15-27 includes, wherein to perform the cut using the robotic surgical device, the processor is further to contour or perform a fine cut or burr to create a flat surface on the bone or to prepare a canal for a stem using the robotic surgical device.

Example 29 is a system for performing a robotic revision knee arthroplasty, the system comprising: a robotic surgical device; and a processor, communicatively coupled to the surgical robot, the processor configured to: intraoperatively receive a plurality of reference points of a previously implanted implant; determine information about an existing implant using the reference points; plan a cut to remove the existing implant based on the information; perform the cut using a robotic surgical device; and replan for a new implant based on the cut.

In Example 30, the subject matter of Example 29 includes, wherein the processor is further to cause the robotic surgical device to install the new implant.

In Example 31, the subject matter of Examples 29-30 includes, wherein the processor is further to receive the reference points from an optical navigation device.

In Example 32, the subject matter of Examples 29-31 includes, wherein the processor is further to cause the robotic surgical device to prepare a canal for the new implant.

In Example 33, the subject matter of Examples 29-32 includes, wherein to receive the plurality of reference points, the processor is further to generate the reference points from identifiable portions of an x-ray.

In Example 34, the subject matter of Examples 29-33 includes, wherein to receive the plurality of reference points, the processor is further to receive the plurality of reference points via registering the plurality of reference points on the existing implant intraoperatively.

In Example 35, the subject matter of Examples 29-34 includes, wherein the information about the existing implant includes at least one of an implant type, a maker of the implant, degradation information about the implant, or a failure reason for the implant.

In Example 36, the subject matter of Examples 29-35 includes, wherein to plan the cut, the processor is further to predict a surface for the new implant.

In Example 37, the subject matter of Examples 29-36 includes, wherein to perform the cut, the processor is further to configure the robotic surgical device as a robotic cut guide.

In Example 38, the subject matter of Examples 29-37 includes, wherein to perform the cut, the processor is further to cause the robotic surgical device to perform the cut automatically.

In Example 39, the subject matter of Examples 29-38 includes, wherein to replan for the new implant, the processor is further to use predictive analytics or a bone atlas.

In Example 40, the subject matter of Examples 29-39 includes, wherein the processor is further to plan a clean-up cut after the cut is performed.

In Example 41, the subject matter of Examples 29-40 includes, wherein to perform the cut using the robotic surgical device, the processor is further to cut under the existing implant using the robotic surgical device.

In Example 42, the subject matter of Examples 29-41 includes, wherein to perform the cut using the robotic surgical device, the processor is further to contour or perform a fine cut or burr to create a flat surface on the bone or to prepare a canal for a stem using the robotic surgical device.

Example 43 is at least one machine-readable medium including instructions that, when executed by processing circuitry, cause the processing circuitry to perform operations to implement of any of Examples 1-42.

Example 44 is an apparatus comprising means to implement of any of Examples 1-42.

Example 45 is a system to implement of any of Examples 1-42.

Example 46 is a method to implement of any of Examples 1-42.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for using a robotic device during a revision knee arthroplasty on a patient, the system comprising:

- a robotic surgical device;
- processing circuitry, communicatively coupled to the robotic surgical device; and
- memory, including instructions, which when executed by the processing circuitry, causes the processing circuitry to:
- receive data from the robotic surgical device during a revision knee arthroplasty, the data including sensor data of a knee of a patient during the revision knee arthroplasty;
- process the data to identify at least one anatomical landmark;
- estimate, based on the at least one anatomical landmark, a plurality of potential joint lines using a machine learning trained model;
- display on a user interface, at least one joint line of the plurality of potential joint lines, wherein the at least one joint line is displayed in response to a surgeon selection of the at least one joint line on a display including the plurality of potential joint lines; and
- cause the robotic surgical device to perform a surgical step of the revision knee arthroplasty based on the at least one joint line.

2. The system of claim 1, wherein the instructions further include instructions to extrapolate missing bone structure from the at least one anatomical landmark and a reference model to determine the at least one joint line.

3. The system of claim 1, wherein the at least one joint line is determined by comparing existing patient anatomy to an atlas of x-ray data.

4. The system of claim 1, wherein the at least one anatomical landmark is an epicondyle landmark.

5. The system of claim 1, wherein the at least one joint line is a contra-lateral joint line determined using information from another knee of the patient.

6. The system of claim 1, wherein the at least one joint line is displayed in response to a surgeon selection of the at least one joint line on a display including the plurality of potential joint lines.

7. The system of claim 1, wherein the at least one joint line is a joint line of the plurality of potential joint lines having a highest probability estimated using robotic measurements of landmarks of the knee of the patient.

8. The system of claim 1, wherein the machine learning trained model is trained to use labeled atlas images to generate a model of the knee of the patient.

9. The system of claim 1, wherein the instructions further include instructions to identify an implant being replaced during the revision knee arthroplasty and using the implant identified as a calibration or for navigation to determine a location of the at least one anatomical landmark in the knee of the patient.

10. The system of claim 1, wherein the instructions further include instructions to plan a tibial surface to be automatically burred by the robotic surgical device.

11. The system of claim 1, wherein the instructions further include instructions to:

intraoperatively receive reference points of an existing implant corresponding to the knee of the patient;

determine information about the existing implant using the reference points;

plan a cut on a bone of the knee of the patient to remove the existing implant based on the information;

cause the robotic surgical device to perform the cut on the bone;

cause the robotic surgical device to be configured to automatically apply a force, via an impaction device coupled to an end effector of the robotic surgical device, in line with an axis of a canal of the bone by constraining a direction of an impaction on the bone by the impaction device along the axis of the canal; and replan for a new implant based on the cut.

12. At least one non-transitory machine readable medium, including instructions for using a robotic surgical device during a revision knee arthroplasty on a patient, which when executed by processing circuitry, cause the processing circuitry to:

receive data from the robotic surgical device during a revision knee arthroplasty, the data including sensor data of a knee of the patient during the revision knee arthroplasty;

process the data to identify at least one anatomical landmark;

estimate, based on the at least one anatomical landmark, a plurality of potential joint lines using a machine learning trained model;

display on a user interface, at least one joint line of the plurality of potential joint lines, wherein the at least one joint line is displayed in response to a surgeon selection of the at least one joint line on a display including the plurality of potential joint lines; and cause the robotic surgical device to perform a surgical step of the revision knee arthroplasty based on the at least one joint line.

13. The at least one non-transitory machine readable medium of claim 12, wherein the instructions further include instructions to extrapolate missing bone structure from the at least one anatomical landmark and a reference model to determine the at least one joint line.

14. The at least one non-transitory machine readable medium of claim 12, wherein the at least one joint line is determined by comparing existing patient anatomy to an atlas of x-ray data.

15. The at least one non-transitory machine readable medium of claim 12, wherein the at least one anatomical landmark is an epicondyle landmark.

16. The at least one non-transitory machine readable medium of claim 12, wherein the at least one joint line is a contra-lateral joint line determined using information from another knee of the patient.

17. The at least one non-transitory machine readable medium of claim 12, wherein the at least one joint line is displayed in response to a surgeon selection of the at least one joint line on a display including the plurality of potential joint lines.

18. The at least one non-transitory machine readable medium of claim 12, wherein the at least one joint line is a joint line of the plurality of potential joint lines having a highest probability estimated using robotic measurements of landmarks of the knee of the patient.

* * * * *